United States Patent
Wang et al.

(10) Patent No.: US 10,344,358 B2
(45) Date of Patent: Jul. 9, 2019

(54) METHOD TO INCORPORATED SKIN AND CORE MATERIAL PROPERTIES IN PERFORMANCE ANALYSIS OF HIGH PRESSURE DIE CASTING ALUMINUM COMPONENTS

(71) Applicant: GM Global Technology Operations LLC, Detroit, MI (US)

(72) Inventors: Qigui Wang, Rochester Hills, MI (US); Bing Li, Rochester Hills, MI (US); Cherng-Chi Chang, Troy, MI (US); Wenying Yang, Rochester Hills, MI (US); Michael J. McCreedy, Fenton, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 1001 days.

(21) Appl. No.: 14/547,308

(22) Filed: Nov. 19, 2014

(65) Prior Publication Data
US 2016/0138912 A1 May 19, 2016

(51) Int. Cl.
| C22C 21/02 | (2006.01) |
| G06F 17/50 | (2006.01) |
| B22D 11/00 | (2006.01) |

(52) U.S. Cl.
CPC ............ *C22C 21/02* (2013.01); *B22D 11/006* (2013.01); *G01N 2223/628* (2013.01); *G06F 17/5018* (2013.01)

(58) Field of Classification Search
CPC .. G01B 21/08; G01B 21/045; B65H 2220/03; G06F 17/5018; G06F 2217/41; C22C 21/02
See application file for complete search history.

(56) References Cited

U.S. PATENT DOCUMENTS

| 8,666,706 B2 | 3/2014 | Zhou et al. | |
| 2005/0107994 A1* | 5/2005 | Wan | G06T 17/20 |
| | | | 703/2 |

OTHER PUBLICATIONS

Quan et al. Geometric analysis of Casting Components, and World Congress on Integrated Computational Materials Engineering, TMS (The Minerals, Metals & Materials Society) 2013, pp. 105-106.*

(Continued)

*Primary Examiner* — Matthew S Smith
*Assistant Examiner* — Steven B Gauthier

(57) ABSTRACT

A method, device and article of manufacture for determining properties in a high pressure die cast component. Upon receipt of geometric information that corresponds to a location of interest within the component, a ray-triangle intersection relationship is used to calculate a wall thickness of the location of interest; this relationship is simplified by being used in conjunction with an octree-based relationship. One or more calculations are performed to determine a skin thickness based on the calculated wall thickness, and the skin thickness calculations are based on at least one of a logarithmic relationship, a polynomial relationship and a power law relationship. Changes in component shape or size may be taken into consideration to adjust the remaining skin layer thickness, such as that when the as-cast component is exposed to subsequent machining or related post-casting operations. From this, the properties are mapped to allow node-by-node variations in mechanical properties based on whether the node resides in the component skin region or core region.

7 Claims, 9 Drawing Sheets

(56) References Cited

OTHER PUBLICATIONS

Hatch, Aluminum properties and Physical Metallurgy, American Society for Metals, 1984, pp. 32-34.*

* cited by examiner

METHOD TO INCORPORATED SKIN AND CORE MATERIAL PROPERTIES IN PERFORMANCE ANALYSIS OF HIGH PRESSURE DIE CASTING ALUMINUM COMPONENTS

BACKGROUND OF THE INVENTION

This invention is related generally to the quantification of properties in high pressure die cast (HPDC) aluminum alloy components, and particularly to a way to determine material properties in such cast components by taking into consideration both skin and core properties.

HPDC (also referred to as die casting) is being used extensively in the production of lightweight aluminum alloy components in general, and particularly for automotive components, such as engine blocks and transmission cases, as well as pistons or suspension parts. Low costs for large-scale production, close dimensional tolerances (near-net-shape) and smooth surface finishes are all positive attributes that make HPDC so attractive. Unlike alloys (such as 319 or 356) that are not typically used in HPDC, certain aluminum alloys, such as 380, 383, 390 or the like, are particularly well-suited to HPDC for their cost, strength, fluidity and generally good corrosion resistance qualities.

Die casting components generally form an outer skin region or layer that surrounds an internal core region or layer. In general, the material properties associated with the skin tend to be superior to those in the core, where the skin region has an abundance of relatively defect-free, dense microstructure while the core region has a higher concentration of voids, porosity and related defects. Testing for commonly-used figures of merit has shown that the skin region of a cast aluminum alloy component may exhibit up to 15% higher tensile strengths and over 80% more ductility that the core region. In typical cast components, the skin can be between about 100 microns and a couple of millimeters thick, depending on the size and geometry of the component.

In practice, it is difficult to characterize the properties of the skin separately from those of the core. This in turn negatively impacts the ability of the component designer to optimize the design for efficient and reliable operation, where the use of analytical tools (such as finite element techniques) of HPDC components often eschews the location-specific nature of the mechanical properties in favor of assuming the presence of uniform microstructure and properties across the entirety of the cast component.

One approach to more accurately determine the skin layer thickness for a given component is discussed in co-pending U.S. patent application Ser. No. 14/253,119 that was filed on Apr. 5, 2014 and owned by the Assignee of the present application and incorporated in its entirety by reference. The approach discussed therein uses a metallographic technique that takes advantage of changes in the volume fraction of eutectic phases in general, and more particularly where cooling and diffusion dynamics act as a way to help determine where this change occurs. As with all metallographic techniques, it relies upon sensed images (such as those made with a microscope or other magnification device, where the surface of the component being sensed has been prepared to better highlight the microstructural features that may help delineate where different material properties (such as those between the aforementioned core and skin regions) may be present. While such an approach offers significant improvements in determining skin layer thickness, there still remains a need to have a more automated way to correlate the skin layer thickness to a local wall thickness for a given component to automate the determination of skin layer thickness in HPDC components so that metallographic or related additional data-gathering techniques are not required.

SUMMARY OF THE INVENTION

According to a first aspect of the present invention, a method of using both skin and core material properties in the performance analysis of an HPDC metal casting is disclosed. In particular, the present approach allows the accurate determination of component durability properties (such as fatigue, strength and related mechanical indicia) of HPDC aluminum components by taking into consideration different materials properties for a casting component's skin and core regions. Part of the present invention takes advantage of the fact that engineering models (for example, computer-aided design (CAD), finite element or related files) have already been created by the designer and/or CAE analysis engineer; as such, accurate geometric representations of the component being modeled can be used by a particularly-configured data processor in order to expedite the analysis proposed herein. As such, the present invention permits the incorporation of both the skin and core material properties into an analytical model that helps designers predict mechanical property information, component performance and durability with a high degree of accuracy without having to resort to metallographic or other measurement-based tehniques. This leads to quicker design turnaround times for HPDC aluminum components (such as engine blocks and transmission cases), as well as reduces the overall cost of intergrating the component into an overall system design.

Initially, a ray triangle intersection method together with an octree-based algorithm accurately determines wall thickness or related local geometry of a particular portion of an HPDC component based on the overall thickness knowledge that can be taken from the aforementioned engineering models. From this, the skin layer thickness may be correlated to the local wall thickness by using empirically-observed polynomial, logarithmic or power law relationships. From this, adjustments are made to the skin layer to account for one or more post-casting operations (such as machining or other surface layer removal or modification activities) that are used to place the as-cast component into a more finished form. Lastly, nodal property mapping operations are performed in order to assign specific material property information to each node of the skin and core regions of the component being evaluated.

In the present context, the terms "mechanical property information", "material property information" and their variants are meant to encompass all such structural properties that are inherent in the component (or portion thereof) by virtue of the constituent material being used, as well as any subset of such properties that are needed in order to perform the calculations that are discussed in more detail below. As such, the term is used herein to define commonly accepted engineering properties that would need to be considered during the course of designing a particular structural component; such properties may include (but are not limited to) strength (compressive, tensile, shear, etc.), temperature, density, hardness, modulus of elasticity, roughness, fatigue, electrical and thermal conductivity, coefficient of thermal expansion or the like. These properties are well-known for many aluminum-based alloys in general (for example, 319, 356, 357, 380, 390, 393 or the like) as well as the subset of those that are particularly compatible with HPDC techniques. Such information may be provided such that it can be operated upon by the algorithms to the present invention through well-known means, such as lookup tables, computer-readable memory or other structured data input.

According to another aspect of the present invention, a method of determining the mechanical or related structural properties in a cast component is disclosed. The method includes using a particularly-configured computer to receive geometric information pertaining to a location of interest within the component, using the computer to determine a ray-triangle intersection relationship to calculate a wall thickness of the location of interest, and using the computer to calculate the skin thickness based on the wall thickness. As with the previous aspect, a correlation between the skin and wall thicknesses is based on at least one of a logarithmic relationship, a polynomial relationship and a power law relationship. Also as with the previous aspect, the ray-triangle intersection relationship includes using an octree-based relationship to reduce the number of triangles analyzed within the location of interest by the ray-triangle intersection relationship. In the present context, the location of interest may form a part of the overall component, or (at least in cases where the component is defined by a geometrically simple shape) possibly a substantial entirety of the component. As with the previous aspect, adjustments are made to the skin layer to account for one or more post-casting operations, after which mapping operations are performed in order to assign specific material property information to each node of the skin and core regions of the component being evaluated.

According to yet another aspect of the present invention, an article of manufacture is disclosed. The article includes a computer usable medium having computer readable program code embodied therein for determining skin thicknesses in an HPDC component is disclosed. The program code includes a portion for causing the computer to accept data pertaining to geometric information of a location of interest within the component, a portion for causing the computer to generate wall thickness data based on a ray-triangle intersection relationship, a portion for causing the computer to generate the skin thickness based on the wall thickness where the correlation between the skin and wall thicknesses is based on at least one of a logarithmic relationship, a polynomial relationship and a power law relationship, and a portion for causing the computer to produce an output that corresponds to the skin thickness. As with the previous aspects, an octree-based relationship is used to simplify (i.e., reduce) the number of triangles analyzed within the location of interest by the ray-triangle intersection relationship. Adjustments are made to the skin layer to account for one or more post-casting operations, and then nodal property mapping is performed to assign specific material properties to each node according to node characteristics of the respective skin and core nodes.

BRIEF DESCRIPTION OF THE DRAWINGS

The following detailed description of the preferred embodiments of the present invention can be best understood when read in conjunction with the following drawings, where like structure is indicated with like reference numerals and in which.

DETAILED DESCRIPTION OF THE PREFERRED EMBODIMENTS

Figure 1:
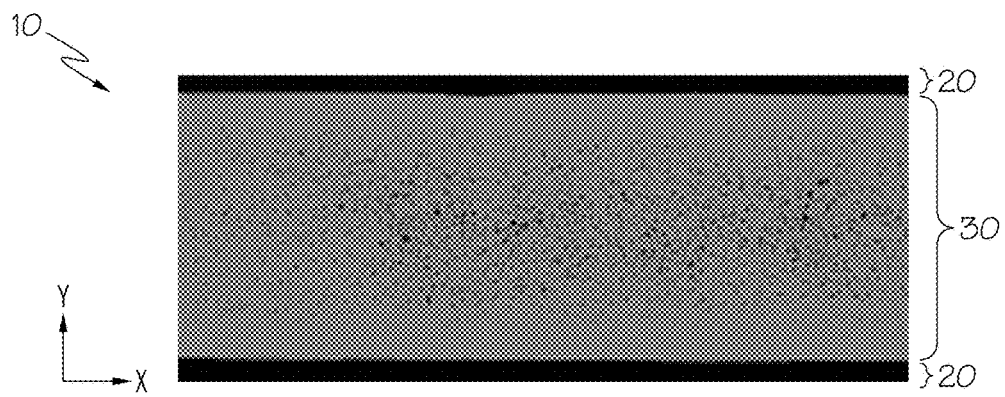
FIG. 1 shows a notional component made with HPDC showing representative skin and core regions.
Figure 2A:
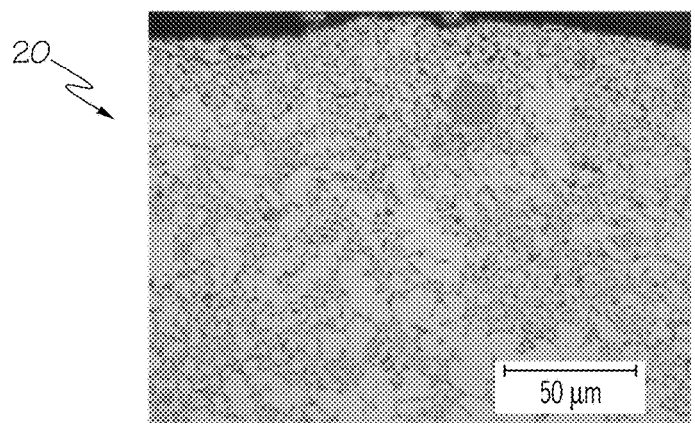
FIGS. 2A and 2B show respective micrographs of the skin and core regions of the component of FIG. 1.
Figure 2B:
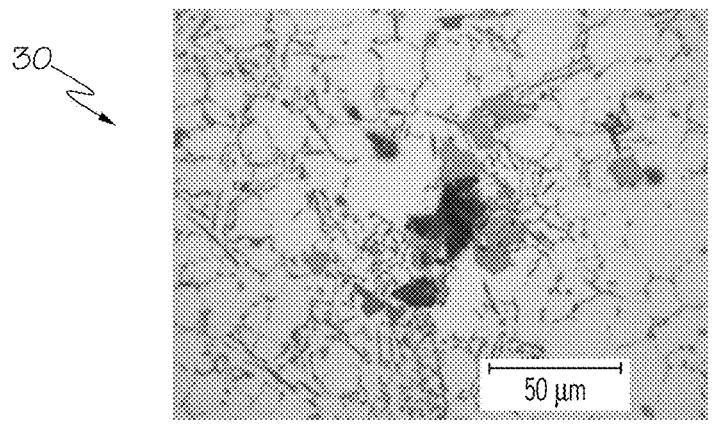

Referring first to FIGS. 1, 2A and 2B, a notional object to be analyzed by the method of the present invention is in the form of an HPDC cast component 10 that shows an exterior skin region 20 and an interior core region 30. In the example shown, the total thickness along the vertical (i.e., y) axis is about 19 millimeters, while the top and bottom skin regions 20 each account for about 2.67 millimeters of the overall thickness that corresponds to the wall thickness $T_W$ for the location of interest within the component 10. As can be seen, there is significantly more porosity in the core region 30 than in the skin regions 20 where the higher porosity of the core region 30 results in generally lower mechanical properties than in the lower porosity skin region 20. Referring with particularity to FIGS. 2A and 2B, micrographs of an HPDC A380 aluminum alloy are shown, where porosity and related voids are much more pronounced in the core region of FIG. 2B than in the skin region of FIG. 2B.

One way to think of the present invention is as a four-step general process. Regarding the first two of these steps and referring next to FIGS. 3A through 3G, a determination of local wall thickness $T_W$ of a particular component in its as-cast state is made, after which a skin (also called skin layer) thickness $T_{SL}$ is derived based on the determined wall thickness $T_W$ from the first step. In particular, it uses a combination of a ray triangle intersection method and an octree data structure. As it is time consuming and inefficient to check a ray that is shot from a particular point of interest with each triangle on the surfaces in an object, it is necessary to filter out the triangles that don't intersect with the ray. This can be done by using an octree-based algorithm, where all triangles are put into different leaf nodes (that correspond to the smallest subdivided space within a cube in the octree data structure) as will be discussed in more detail below) of an octree according to their bounding boxes $B_T$. If a ray r intersects with the node N, it may intersect with the triangles in the node N without consideration of other external triangles. The determination of the local interior or exterior wall thickness discussed herein is important in that it allows determination of the wall thickness of the entire component. The third and fourth steps will be described in more detail below.

As a threshold matter, it is important to first define what is meant by the wall thickness $T_W$ in an HPDC casting.

Figure 3A:
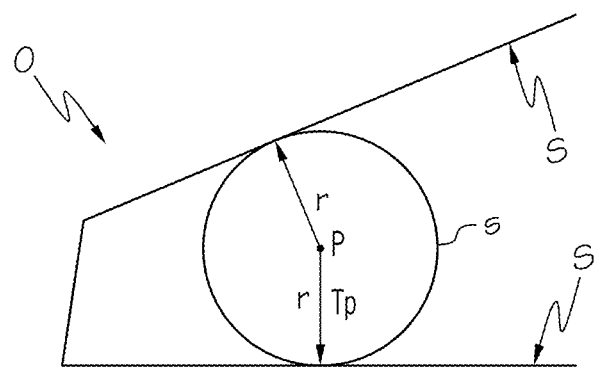
FIGS. 3A through 3G show respectively an interior wall thickness at a point inside an object being analyzed, an exterior wall thickness at a point outside an object being analyzed, a recursive subdivision of the object into a cube and the cube into octants on one side and a corresponding octree on the other side, an axis-aligned bounding box of a notional cylindrically-shaped object, a notional triangle used to build a ray triangle intersection model, a selected triange and neighbor triangles, and a plot of an octree-based algorithm that takes advantage of triangle intersections to determine the geometric features of an as-cast component.

Within the present context, two generic definitions of the wall thickness $T_W$ may be used; one corresponds to the interior wall thickness for points inside an object, while the other corresponds to the exterior wall thickness for points on the object surface. Referring with particularity to FIG. 3A, the interior wall thickness at a point P inside an object O that is part of HPDC component 10 is defined as twice the minimum distance from that point P to the nearest surface S of the object O. Its value can be obtained by growing a sphere s or by omnidirectionally projecting rays r from point P along towards the surface S of object O. The shortest ray r length (i.e., the distance between point P and surface S) gives the wall thickness $T_W$ at that point P. This definition is mainly for the maximum wall thickness calculation.

Figure 3B:
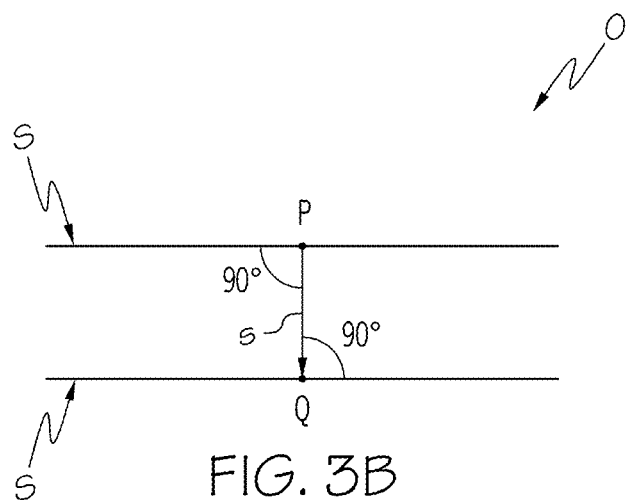

Referring with particularity to FIG. 3B, the exterior wall thickness at point P on the portion of the object O surface S that makes up a particular location of interest is defined as the distance between P and Q. Using the ray triangle intersection method, a simulated ray r is projected from point P on the surface S in a direction opposite to the local outwards surface S normal at point Q, to which intersects the immediately opposite surface S of the object O. It will be appreciated that this definition is mainly for the minimum wall thickness calculation, and that it is effective only when the opposing surfaces S are parallel.

Figure 3C:
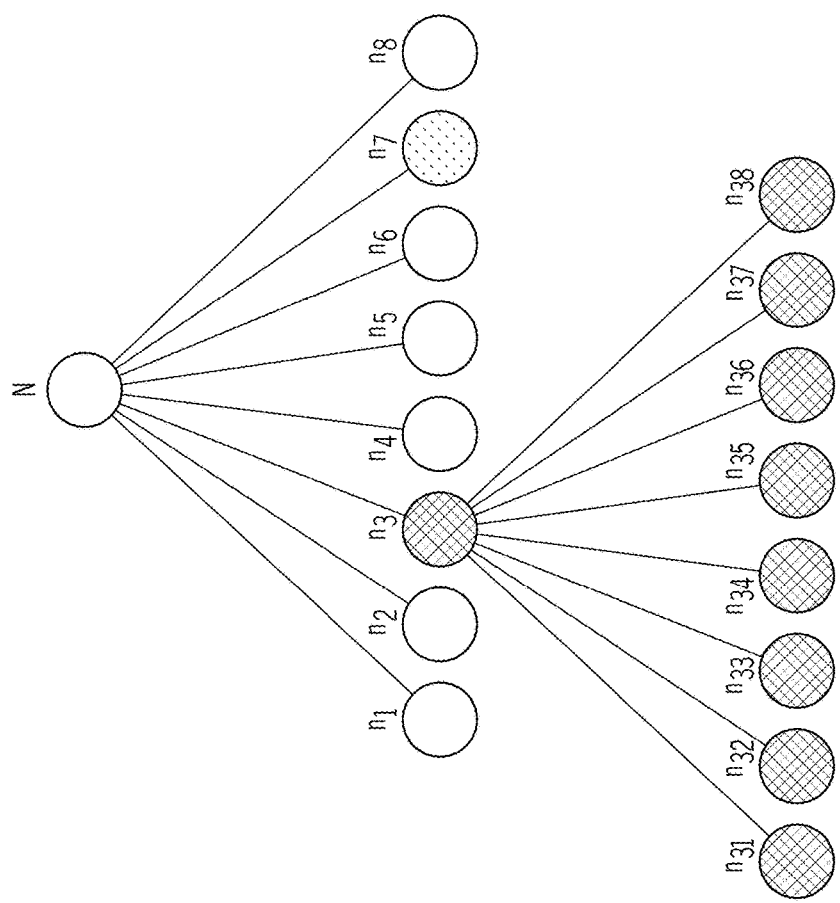
Figure 3C:
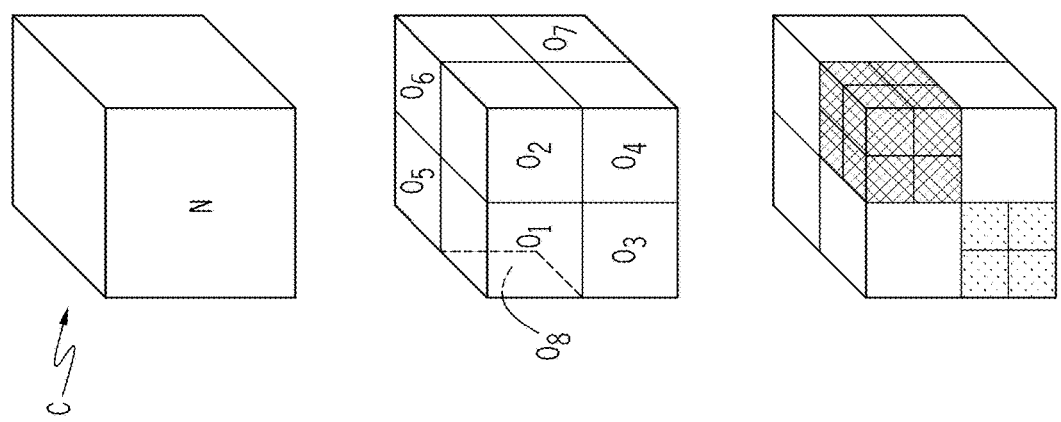

An octree data structure is one in which each internal node has exactly eight children except for the leaf node. As shown in FIG. 3C, each node $N_C$ in an octree subdivides the space into eight octants $o_1$ through $o_8$ such that the node $N_C$ corresponds to a cube C in space. In other words, node $N_C$ defines the central node of cube C. There are also eight subnodes $n_1$ through $n_8$ that define the central nodes of eight subdivided octants $o_1$ through $o_8$ from cube C; these are defined as the octree nodes $N_O$; these also form the children nodes of central node $N_C$. Likewise (by way of example), nodes $n_{31}$ through $n_{38}$ at the bottom of the octree are the central subnodes of eight subdivided cubes when an exemplary octree node $N_O$ (the present example of which—$n_3$—corresponds to octant $o_3$) acts as a central node; these subnodes $n_{31}$ through $n_{38}$ are considered to be leaf nodes $N_L$ in that they do not have any children nodes; this is depicted in the figure. In the present context, the leaf nodes $N_L$ are those that correspond to the smallest subdivided spaces. In order to add triangles to an octree, each member in a triangle set must be compared with nodes in the octree. For convenience, a bounding box $B_T$ for each triangle is constructed and is used to be compared with nodes instead. Moreover, the bounding box $B_T$ will offer facilities for the ray-triangle intersection test that is discussed in more detail below. In particular, the bounding box $B_T$ is defined as the smallest cuboid (or rectangle in 2D) that fully contains the object O. This is shown as step 130 in FIG. 6.

Figure 3D:
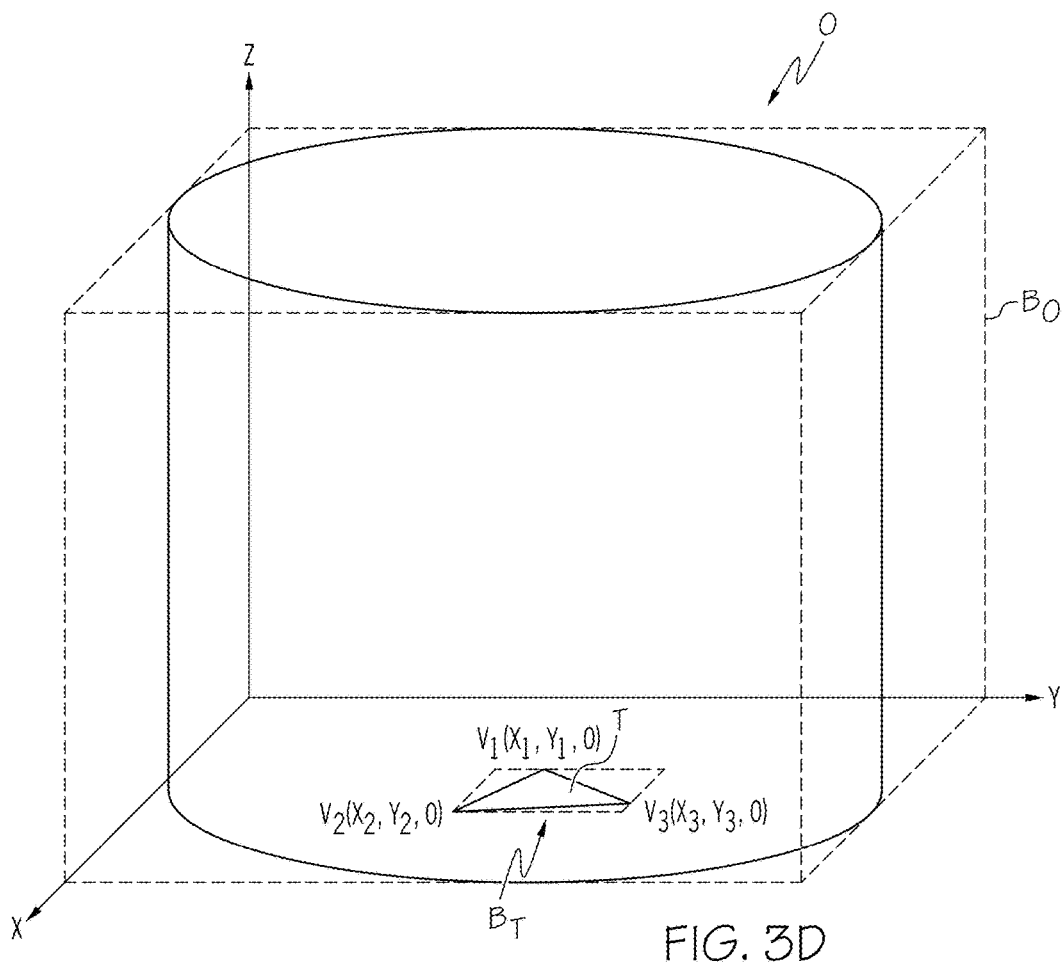

FIG. 3D shows the bounding box $B_O$ within an aligned Cartesian coordinate system where the edges of the box $B_O$ are parallel to coordinate axes to simplify the construction of the box by getting the maximum and the minimum values in respective x, y and z directions. For data pre-processing, all triangles T in the stereolithography (STL) geometric CAD file of the shape of the location of interest within the component being studied are added to the corresponding nodes of the octree. During the process, the algorithm compares the triangle bounding box $B_T$ with the bounding box $B_O$ of the octree node. This is shown as step 110 in FIG. 6.

Figure 3E:
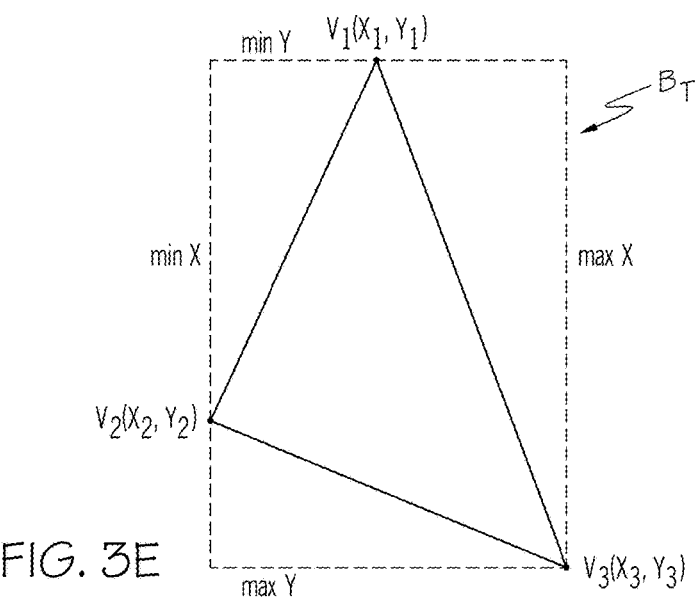
Figure 3F:
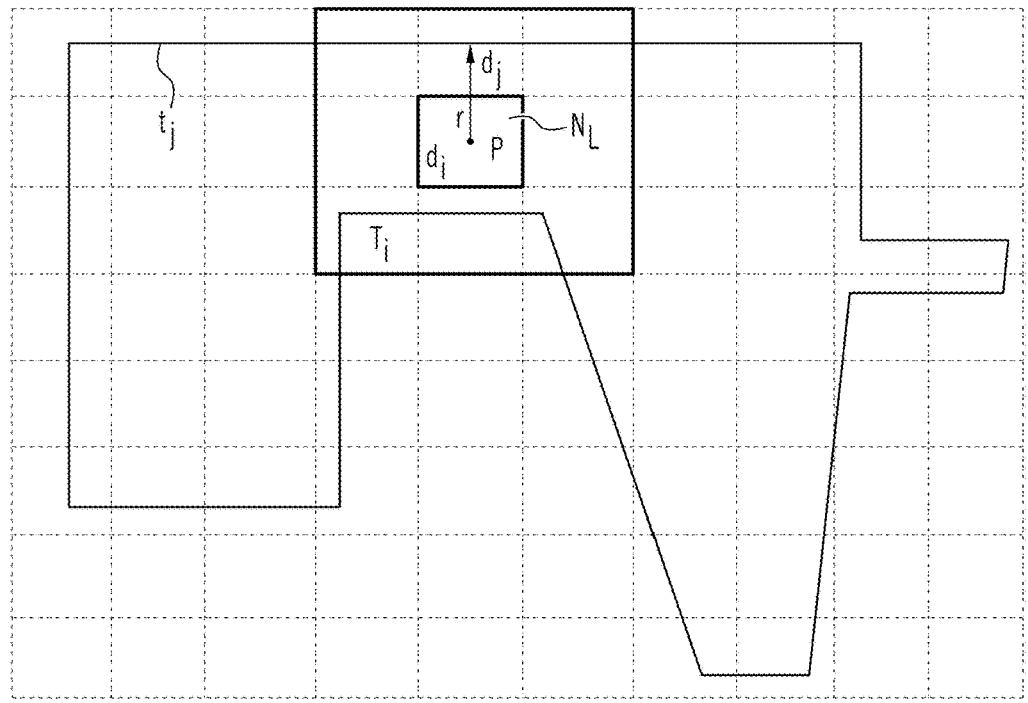
Figure 3G:
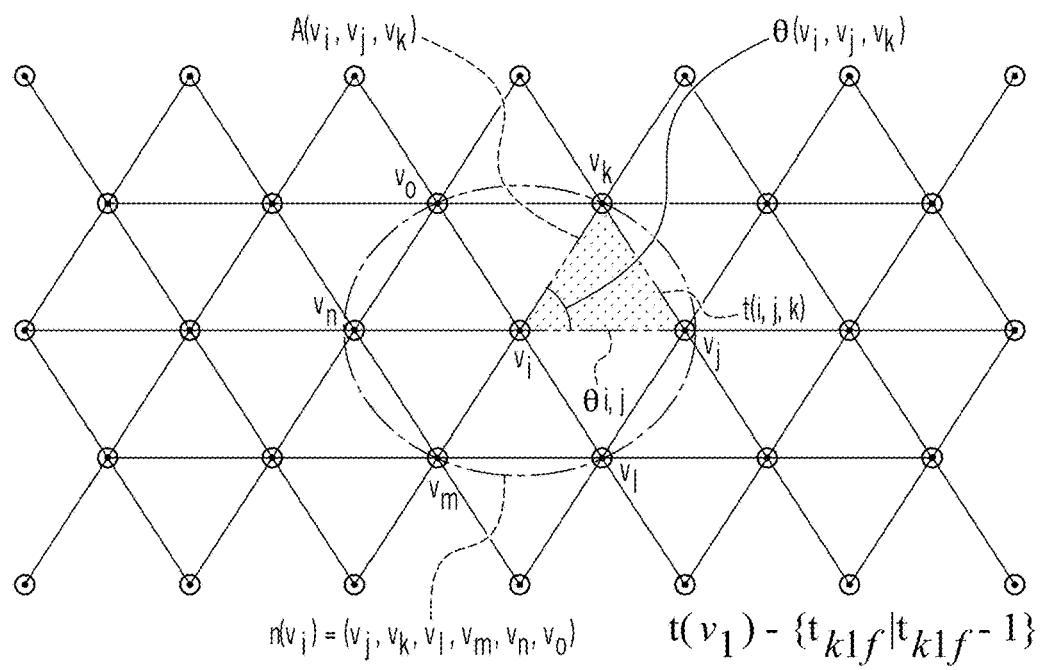
Figure 6:
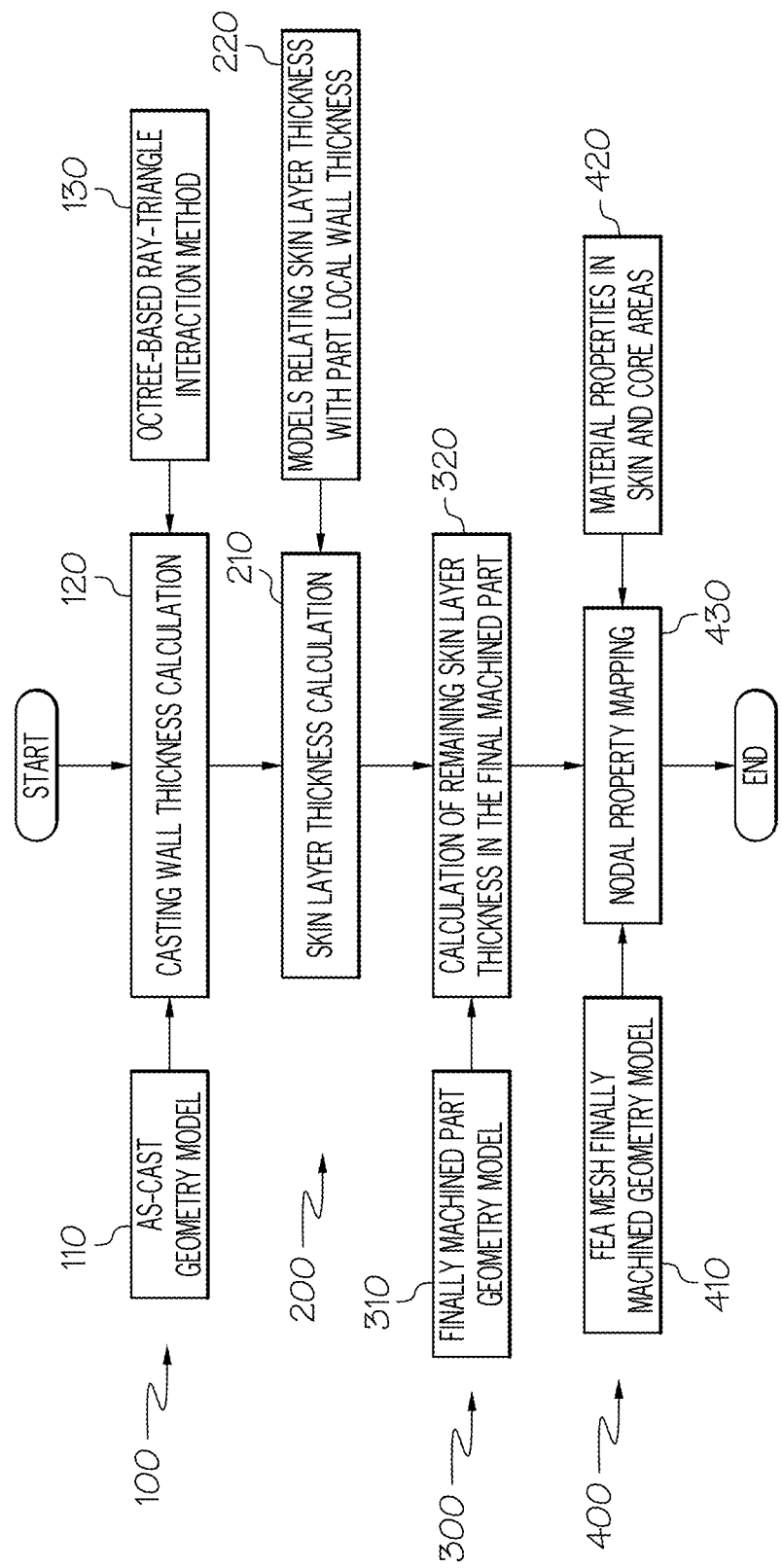
FIG. 6 shows a block diagram depicting the determination of material properties in the skin and core regions of a cast component in accordance with an embodiment of the present invention.

Referring next to FIGS. 3E through 3G in conjunction with FIG. 6, the triangle building process for triangle T of FIG. 3D is shown. If bounding box $B_O$ contains a triangle bounding box $B_T$, then it continues to compare bounding box $B_T$ with the octree node $N_O$ until the depth of the current node is more than or equal to the octree's maximum depth or none of the current node's eight children contains bounding box $B_T$. Then the triangle T is added to the corresponding nodes. After all triangles T are added, an unbalanced octree is completed. After data pre-processing, the candidate triangles T that probably intersect with a ray can be identified by doing a ray-node intersection test. If a node intersects with a ray, its eight children ($t'_i$) are continued to be tested until the current node is a deemed to be a leaf node $N_L$. All candidate triangles are obtained by reading a triangle list of each intersection node during the test. As above, this is shown as step 110 in FIG. 6.

The above are used to perform a wall thickness $T_W$ calculation, where the intersection point must lie on the triangle which is nearest to point P and the ray direction is the normal of the triangle. The direction of the ray can be confirmed by searching the nearest triangle to that of point P. The intersection distance at this location to both surfaces is the wall thickness. To calculate local wall thickness $T_W$, the flag of each node $N_j$ in the octree is first set to a "false" condition by traversing the octree until the leaf node $N_L$ which point P is located, is found. After this leaf node $N_L$ is found, all of the candidate triangles near this node are obtained by searching the leaf node $N_L$. For each candidate triangle $T_j$, a ray r is shot from point P with the direction of $T_j$'s normal, then the intersection distance $d_j$ between $T_j$ and P is computed. The minimum $d_j$ is the distance from point P to the component surface S. If there is no satisfied dj, the searching scope is expanded. At the same time, the candidate triangles T are ascertained by searching the surrounding leaf nodes $N_L$. The rest may be deduced by analogy until the desired dj is arrived upon. The same procedure can be followed to find the minimum distance $d_i$ from the point P to other surface with triangle $T_i$. The sum of the two minimum distances ($d_i+d_j$) is the local wall thickness, as shown with particularity in FIG. 3G. This is shown as step 120 in FIG. 6.

For exterior wall thickness determination, the candidate point P that is used to compute the wall thickness $T_W$ may be around the triangle T. In order to get the exact value of the thickness, the nearest triangle T is searched. A ray r is made from triangle T in a direction opposite to the local outwards surface S normal to intersect the opposite surface S of the object O immediately. The distance between the two surfaces is exactly the wall thickness $T_W$.

Figure 4:
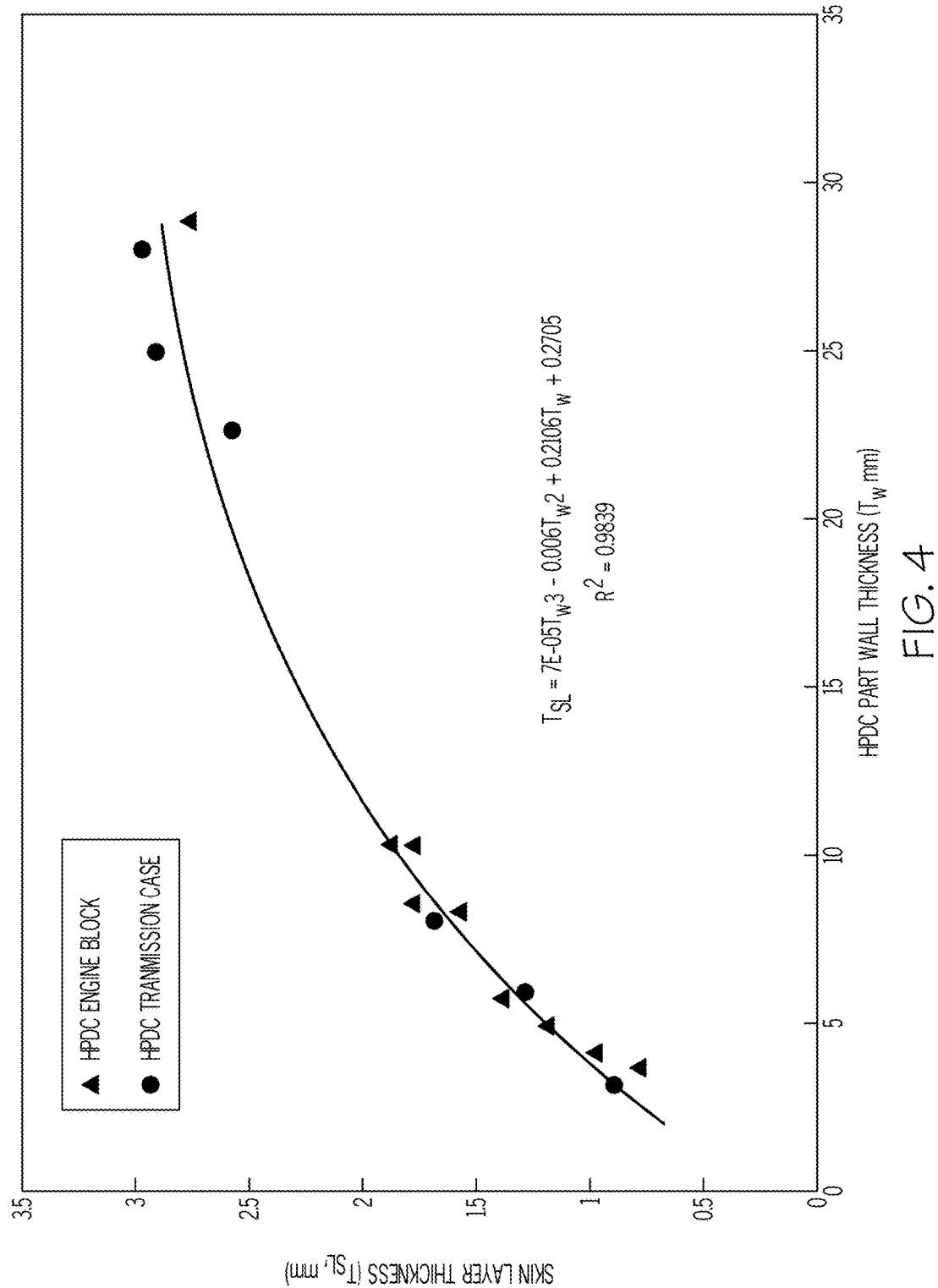
FIG. 4 shows a polynomial correlation between skin layer thickness and part local wall thickness.
Figure 5:
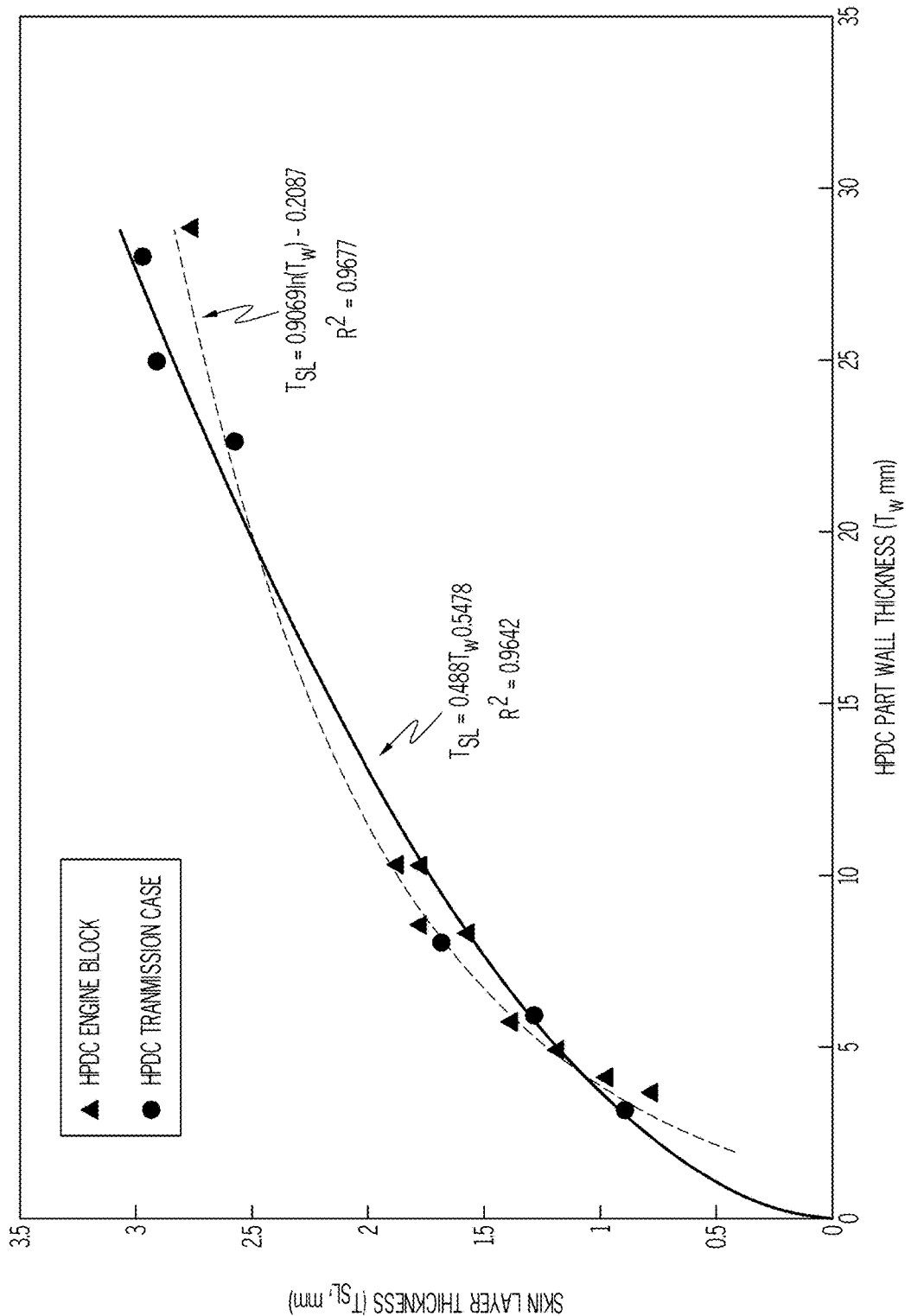
FIG. 5 shows a correlation between skin layer thickness and part local wall thickness represented in a power law formula and a logarithmic formula.

Referring next to FIGS. 4 through 6, once the local wall thickness $T_W$ has been determined for the location of interest within a particular HPDC component by the combination of ray triangle intersection and octree data processing, this value can be used to predict a skin thickness $T_{SL}$ value within the same location within the same part. As alluded to above, in HPDC, the skin layers near the surface if the die or mold cool very fast during solidification; in addition to finer microstructure, lower porosity and fewer other defects compared with the core area, the faster cooling rate in the skin layer also reduces solute diffusion rate in the solidified material (such as aluminum) and increases the solute content in the remaining solidifying liquid. This in turn increases the volume fraction of eutectic phases in the skin layer. In one embodiment, the thickness of the skin layer $T_{SL}$ may be correlated to local part wall thickness $T_W$ as described by the following polynomial.

$$T_{SL}=f(T_W)=7\times10^{-5}T_W^3-0.006T_W^2+0.2162T_W+0.2705 \qquad (1)$$

This is shown with particularity in FIG. 4. Experimental data shows that there is good correlation (where the coefficient of determination (R-squared) is 0.9839 as a measure of the proportion of variability in a data set that is accounted for by a statistical model).

Referring with particularity to FIG. 5, the relationship between skin thickness $T_{SL}$ and part local wall thickness $T_W$ may also be expressed using a power law formula, as depicted by the solid line.

$$T_{SL} = 0.4884 T_W^{0.5478} \quad (2)$$

This relationship may also be expressed as a logarithmic relationship with part local wall thickness $T_W$ (shown presently as a dashed line).

$$T_{SL} = 0.90691 n(T_W) - 0.2087 \quad (3)$$

HPDC (as well as many other) cast components are usually subject to post-cast operations (such as machining) to ensure component shape and size within close tolerances, as well as to have the exposed component surface be suitable for its intended purpose. As a result, some of the skin layer will be fully or partially removed, depending upon the machining or related removal amount and required dimension tolerance. It will be understood by those skilled in the art that machining is frequently a processing step in the manufacture of structural components in order to ensure that the final dimension is within the designed part tolerances, and that because of this, the casting geometry dimension is usually larger than that of the finally machined geometry. After the remaining skin layer thickness is figured out in the finally machined part, the nodal property mapping is conducted using the materials properties for skin and no-skin (i.e., core) areas. Such a process may be carried out in a materials generation program such as described in U.S. Pat. No. 8,666,706 that is owned by the Assignee of the present invention and incorporated herein by reference.

As mentioned above, the present invention involves four general steps, where the first two of these involve a determination of the wall thickness of a particular component in its as-cast state 100, and then a determination of a skin thickness 200. Referring next to FIG. 6, the integration of the first two steps—as well third and fourth steps 300, 400—is shown. Step 300 shows the operations used to determine the final skin layer thickness $T_{SL}$ that remains in the machined surfaces in the finally finished component. For this to happen, the CAD or finite element-based casting geometry model needs to compare with the finally machined geometry model. One way to do that is to first define graph G of a CAD model which is represented by STL format as $$G = \{V, E, T\}$$

where the V denotes the set of vertices $V = \{v_i | v_i = (x_i, y_i, z_i)\}$, i=1, 2, ..., N, N is the number of vertexes, E denotes the set of edges $E = \{e_{ij} | e_{ij} = (v_i, v_j), v_i, v_j \in V, e_{ij} = e_{ji}\}$, i,j=1, 2, ..., N, if $e_{ij}$ is an edge in one triangle, $e_{ij}=1$, $e_{ij}=0$ else. T denotes the set of triangles $T = \{t_{ijk} | t_{ijk} = (v_i, v_j, v_k), v_i \in V, t_{ijk} = t_{jki} = t_{kij}\}$, i,j,k,=1, 2, ..., N, if $t_{ijk}$ is a triangle of the CAD model, $t_{ijk}=1$, otherwise, $t_{ijk}=0$.

Furthermore, let $n(v_i)$ be the set of neighbor vertices $n(v_i) = \{v_j | e_{ij} = 1\}$, j=1, 2, ..., N. In addition, let $t(v_i)$ be the set of neighbor triangles $t(v_i) = \{t_{kij} | t_{kij} = 1\}$, j,k=1, 2, ..., N. Moreover, let $G^{(1)}$ denote the casting CAD model and $G^{(2)}$ denote the machined part CAD model such that the comparison of the two defines the problem of finding a suitable rotation and translation transform which make all vertices set $V^{(2)}$ of $G^{(2)}$ contained in the closed region which is constituted by the triangles set $T^{(1)}$ of $G^{(1)}$. In other words, $$(\alpha', \beta', \gamma', v', \theta', \tau'_\alpha, \tau'_\beta, \tau'_\gamma) = $$
$$\arg\max_{\alpha, \beta, \gamma, \varepsilon, \theta, \tau_\alpha, \tau_\beta, \tau_\gamma} \sum_{i=1}^{N_1} w_i I(t(r(v_i^{(2)}, \alpha, \beta, \gamma, v^{(r)}, \theta), \tau_\alpha, \tau_\beta, \tau_\gamma)),$$
$$s.t. \begin{cases} \alpha^2 + \beta^2 + \gamma^2 = 1, \alpha > 1, \theta < \delta_\theta \\ \tau_\alpha < \delta_x, \tau_\beta < \delta_y, \tau_\gamma < \delta_z \end{cases}.$$

where the $(\alpha, \beta, \gamma, v^{(r)})$ denotes the axis of rotation, i.e.

$$\begin{cases} x = \alpha t + x^{(r)} \\ y = \beta t + y^{(r)} \\ z = \gamma t + z^{(r)} \end{cases} \quad (4)$$

and θ denotes the rotation angle. The direction of rotation is fixed to the positive direction along the straight line by the equation (4) according to the right-hand rule in the counterclockwise direction. The operator r (v,α,β,γ,$v^{(r)}$,θ) lets the vertex v rotated along the positive direction of the line with θ degree; this in turn provides a new vertex v' as follows:

$$v' = r(v, \alpha, \beta, \gamma, v^{(r)}, \theta) \quad (5)$$

where the v' is a rotated vertex of v. The function t(v', $\tau_\alpha$, $\tau_\beta$, $\tau_\gamma$) denotes a translation operator which move the vertex v' with ($\tau_\alpha$, $\tau_\beta$, $\tau_\gamma$), leading to a new vertex v" as follows:

$$v'' = t(v', \tau_\alpha, \tau_\beta, \tau_\gamma) \quad (6)$$

The explicit relationship between v' and v" is described by the following equations:

$$\begin{pmatrix} x'' \\ y'' \\ z'' \\ 1 \end{pmatrix} = \begin{pmatrix} 1 & 0 & 0 & \tau_\alpha \\ 0 & 1 & 0 & \tau_\beta \\ 0 & 0 & 1 & \tau_\gamma \\ 0 & 0 & 0 & 1 \end{pmatrix} \begin{pmatrix} x' \\ y' \\ z' \\ 1 \end{pmatrix} \quad (7)$$

The I(v") is an indicator function:

$$I(v'') = \begin{cases} 1, & \text{if } v'' \in R(G^{(1)}) \\ -1, & \text{else} \end{cases} \quad (8)$$

The $v'' \in R(G^{(1)})$ denotes vertex v" is in the internal of the closed region R which is constituted by the graph $G^{(1)}$. The $w_i$ is the weight of vertex $v_i^{(2)}$, which is calculated as follows:

$$w_i = \frac{\sum_{t_{kij} \in t(v_i)} s(t_{kij}^{(2)})}{s(T^{(2)})} \quad (9)$$

where s(•) denotes the area of one triangle or a group of triangles. This design enables priority movement of the vertex into the internal region of the graph $G^{(1)}$ with larger weight.

The first set of constraint conditions is a constraint of the rotation axis, while the second set of constraint conditions is a constraint on the amount of translation. The two sets of constraints correspond to two sets of basic assumptions. The first of these assumptions is that the object O geometry needs to only take rotation into consideration, while the second is that the object O only goes through simple translation (such as along the x, y or z axis of a Cartesian coordinate system).

After rotating, the objective function and constraints may be further simplified to meet this second assumption. This in turn leads to the following objective function and constraints without considering the rotation operator:

$$(\tau'_\alpha, \tau'_\beta, \tau'_\gamma) = \arg \max_{\alpha,\beta,\gamma,\varepsilon,\theta,\tau_\alpha,\tau_\beta,\tau_\gamma} \sum_{i=1}^{N1} w_i I(t(v_i^{(2)}, \tau_\alpha, \tau_\beta, \tau_\gamma)), \; s.t. \tau_\alpha < \delta_x, \tau_\beta < \delta_y, \tau_\gamma < \delta_z. \quad (10)$$

To solve the optimization problem, it is necessary to first calculate I(•). To judge whether one vertex v is in the region $R(G^{(1)})$ which is constituted by the graph $G^{(1)}$, the relationship between the vertex v and the planes which each triangle $t_{kij}$ lies in needs to be determined. This discretization of the region $R(G^{(1)})$ in turn reduces the complexity of calculating the function $O(N_T^{(1)})$, where the $N_T^{(1)}$ is the number of triangles in $G^{(1)}$.

The as-cast geometry model in STL format 110 is provided. As mentioned above in conjunction with FIG. 3D, the STL geometric CAD file contains the information pertaining to the three points of a selected triangle T in a Cartesian coordinate system. Step 120 calculates a component local wall thickness $T_W$ as discussed above in conjunction with FIG. 3G and the minimum distances from point P to the component surface S. Step 130 shows the octree-based method as discussed above. Step 210 is used to calculate skin layer thickness $T_{SL}$ exemplary results of which are depicted in FIGS. 4 and 5 as discussed above. Step 220 contains models to correlate these thicknesses through the use of Eqns. (1) through (3) mentioned above. Step 310 is used to provide CAD STL files of the finally machined geometry model. This has been mentioned in Eqns. (4) through (9) above. Step 320 is used to perform calculation of remaining skin layer thickness $T_{SL}$ in the finally machined component, also as discussed in Eqns. (4) through (9) above.

Regarding the fourth general step, the nodal properties are mapped so that a detailed understanding of the properties on a node-by-node basis are attained. Step 420 is used to provide the materials properties (such as tensile and fatigue properties) for the exterior skin region 20 and an interior core region 30 of FIG. 1. As mentioned above, the skin tensile strengths (yield strength and ultimate tensile strength) and fatigue strength can be significantly better in the skin region 20 than in the core region 30; the present inventors have recognized improvements of between 10% and 30% Likewise, the ductility of skin region 20 can be 50% to 100% better than the core region 30. Step 430 is the culmination in that it is used to provide nodal property mapping to assign specific properties (such as tensile and fatigue properties) to each node to the FEA meshed finally machined geometry model of step 410. In an alternate configuration, steps 310 and 410 can be combined, depending on the desired format of the information of the geometric model of the component. In FEA meshed geometry model, the meshes on the part surface are all triangles which are similar to those on the CAD model in STL format. In step 310, the geometry model is in CAD STL format, which only has triangles on the surfaces of the part being analyzed. In general, the triangles in CAD STL model are relatively larger compared with FEA models.

Figure 7:
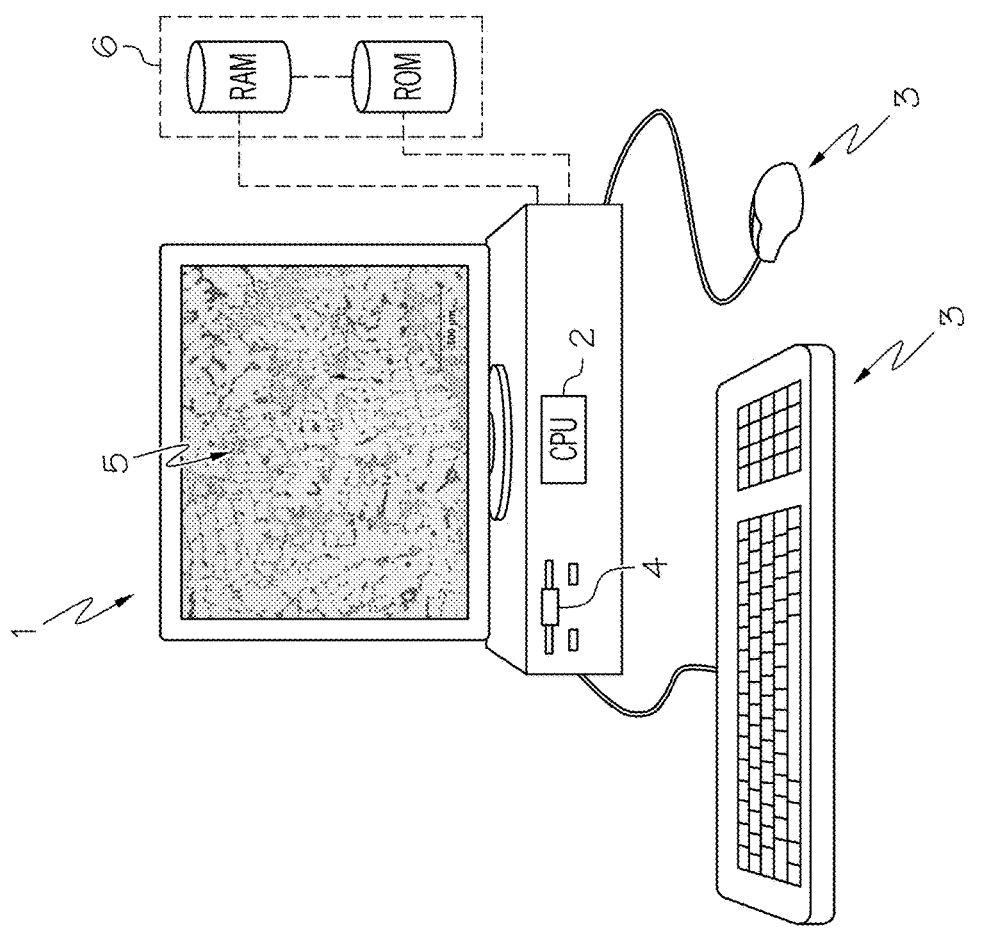
FIG. 7 shows a computerized system that can be used to correlate skin layer thickness and local wall thickness according to an aspect of the present invention.

As mentioned above, one benefit of the present invention is its ability to be implemented in automated data processing equipment, such as that associated with a digital computer. In such case, the automation may take place through a program or related algorithm that can be performed, run or otherwise conducted on the computer. Referring next to FIG. 7, in a preferred form, the digital computer is in the form of a system 10 that preferably includes one or more of an input, an output, a processing unit (often referred to as a central processing unit (CPU)) and memory that can temporarily or permanently store such a code, program or algorithm in the computer's memory such that the instructions contained in the code are operated upon by the processing unit based on input data such that output data generated by the code and the processing unit can be conveyed to another program or a user via output. In one form, a data-containing portion of the memory (also called working memory) is referred to as random access memory (RAM), while an instruction-containing portion of the memory (also called permanent memory is referred to as read only memory (ROM)). A data bus or related set of wires and associated circuitry forms a suitable data communication path that can interconnect the input, output, CPU and memory, as well as any peripheral equipment in such a way as to permit the system to operate as an integrated whole. Such a computer system is referred to as having a von Neumann architecture, and is configured to perform the specific automated steps outlined in this disclosure. As such, system 10 becomes a particularly-adapted computer or computer-related data processing device that employs the salient features of such an architecture in order to perform at least some of the data acquisition, manipulation or related computational functions. It will be appreciated by those skilled in the art that computer-executable instructions that embody the calculations discussed elsewhere in this disclosure can be placed within an appropriate location (such as the aforementioned memory) within system 1 in order to achieve the objectives set forth in the present invention.

System 1 includes a processing unit 2 (which may be in the form of one or more microprocessors or related processing means), one or more mechanisms for information input 3 (including a keyboard, mouse or other device, such as a voice-recognition receiver (not shown)), as well as a one or more loaders 4 (which may be in the form of magnetic or optical memory or related storage in the form of CDs, DVDs, USB port or the like), one or more display screens or related information output 5, a memory 6 and computer-readable program code means (not shown) to process at least a portion of the received information relating to the aluminum alloy. As will be appreciated by those skilled in the art, memory 6 may be in the form of random-access memory (RAM, also called mass memory, which can be used for the temporary storage of data) and instruction-storing memory in the form of read-only memory (ROM). In addition to other forms of input not shown (such as through an internet or related connection to an outside source of data), the loaders 4 may serve as a way to load data or program instructions from one computer-usable medium (such as flash drives or the aforementioned CDs, DVDs or related media) to another (such as memory 6). As will be appreciated by those skilled in the art, system 1 may exist as an autonomous (i.e., stand-alone) unit, or may be the part of a larger network such as those encountered in cloud computing, where various computation, software, data access and storage services may reside in disparate physical locations. Such a dissociation of the computational resources does not detract from such a system being categorized as a computer.

In a particular form, the computer-readable program code that contains the algorithms and formulae mentioned above can be loaded into ROM that is part of memory 6. Such computer-readable program code may also be formed as part of an article of manufacture such that the instructions contained in the code are situated on a magnetically-readable or optically-readable disk or other related non-transitory, machine-readable medium, such as flash memory device, CDs, DVDs, EEPROMs, floppy disks or other such medium capable of storing machine-executable instructions and data structures. Such a medium is capable of being accessed by system 1 or other electronic device having processing unit 2 used for interpreting instructions from the computer-readable program code. Together, the processor 2 and any program code configured to be executed by the processor 2 define a means to perform one or more of the pore size and distribution calculations discussed herein. As will be understood by those skilled in the computer art, system 1 may additionally include additional chipsets, as well as a bus and related wiring for conveying data and related information between processing unit 2 and other devices (such as the aforementioned input, output and memory devices). Upon having the program code means loaded into ROM, system 1 becomes a specific-purpose machine configured to determine HPDC component skin layer thickness properties in a manner as described herein. In another aspect, system 1 may be just the instruction code (including that of the various program modules (not shown)), while in still another aspect, system 1 may include both the instruction code and a computer-readable medium such as mentioned above.

It will also be appreciated by those skilled in the art that there are other ways to receive data and related information besides the manual input approach depicted in input 3 (especially in situations where large amounts of data are being input), and that any conventional means for providing such data in order to allow processing unit 2 to operate on it is within the scope of the present invention. As such, input 3 may also be in the form of high-throughput data line (including the internet connection mentioned above) in order to accept large amounts of code, input data or other information into memory 6. The information output 5 is configured to convey information relating to the desired casting approach to a user (when, for example, the information output 5 is in the form of a screen as shown) or to another program or model. It will likewise be appreciated by those skilled in the art that the features associated with the input 3 and output 5 may be combined into a single functional unit such as a graphical user interface (GUI).

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. Moreover, the term "substantially" is utilized herein to represent the inherent degree of uncertainty that may be attributed to any quantitative comparison, value, measurement, or other representation. As such, it may represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An article of manufacture comprising a computer usable medium having computer readable program code embodied therein for determining skin thickness in a high pressure die cast component, said computer readable program code in said article of manufacture comprising:
   computer readable program code portion for causing said computer to accept data pertaining to geometric information of a location of interest within said component;
   computer readable program code portion for causing said computer to generate wall thickness data based on a ray-triangle intersection relationship that further uses using an octree-based relationship to reduce the number of triangles analyzed within said location of interest by said ray-triangle intersection relationship; and
   computer readable program code portion for causing said computer to generate said skin thickness based on said wall thickness, wherein a correlation between said skin and wall thicknesses is based on at least one of a logarithmic relationship, a polynomial relationship and a power law relationship;
   computer readable program code portion for causing said computer to adjust said determined skin thickness to take into consideration at least one post-casting operation performed on said component; and
   computer readable program code portion for causing said computer to map material property information using a stereolithography computer-aided design model to represent said location of interest by a plurality of triangles defined by edges and vertices, wherein said material property information comprises said determined wall thickness and said adjusted skin thickness at said multiple discrete locations that correspond to said received geometric information.

2. The article of manufacture of claim 1, wherein said computer readable program code portion for causing said computer to accept geometric information is configured to receive said information formatted in at least one of computer-aided design data, computer-aided manufacturing data, computer-aided engineering data and finite-element data form.

3. The article of manufacture of claim 1, wherein said article defines a computer memory.

4. The article of manufacture of claim 3, wherein said computer memory is cooperative with a data input, a data output and a processor such that said data pertaining to geometric information of a location of interest within said component is received through said input, while said output that corresponds to said skin thickness is delivered to said data output.

5. The method of claim 1, wherein said logarithmic relationship is defined by the following:

$$T_{SL}=0.9069 \ln(T_W)-0.2087$$

where $T_{SL}$ is said skin thickness and $T_W$ is said wall thickness.

6. The method of claim 1, wherein said power law relationship is defined by the following:

$$T_{SL}=0.4884 T_W^{0.5478}$$

where $T_{SL}$ is said skin thickness and $T_W$ is said wall thickness.

7. The method of claim 1, wherein said polynomial relationship is defined by the following:

$$T_{SL}=7E-5T_W^3-0.006T_W^2+0.2162T_W+0.2705.$$

* * * * *